United States Patent [19]

Thaler et al.

[11] Patent Number: 5,006,147
[45] Date of Patent: * Apr. 9, 1991

[54] BIODEGRADABLE BARRIER FILMS OF IONOMER POLYMER

[75] Inventors: Warren A. Thaler, Flemington; Pacifico V. Manalastas, Edison; Evelyn N. Drake, Lebanon; Robert D. Lundberg, Bridgewater, all of N.J.

[73] Assignee: Exxon Research and Engineering Company, Florham Park, N.J.

[*] Notice: The portion of the term of this patent subsequent to May 3, 2005 has been disclaimed.

[21] Appl. No.: 380,940

[22] Filed: Jul. 17, 1989

Related U.S. Application Data

[63] Continuation-in-part of Ser. No. 131,583, Dec. 11, 1987, which is a continuation-in-part of Ser. No. 883,533, Jul. 9, 1986, Pat. No. 4,741,956.

[51] Int. Cl.$^5$ ............................................. C05G 3/00
[52] U.S. Cl. ..................................... 71/27; 71/64.02
[58] Field of Search ............................ 71/3, 27, 64.02; 525/186, 190

[56] References Cited

U.S. PATENT DOCUMENTS

| 4,421,898 | 12/1983 | Lundberg et al. | 525/186 |
| 4,741,956 | 5/1988 | Thaler et al. | 71/64.02 |

Primary Examiner—Ferris H. Lander
Attorney, Agent, or Firm—Richard E. Nanfeldt

[57] ABSTRACT

An encapsulated water soluble fertilizer which comprises a polymeric film of about 2 to about 100 micrometers coated on a surface of said fertilizer, said polymeric film comprising a sulfonated polymer having about 10 to about 200 meq of sulfonate groups per 100 grams of said sulfonated polymer, said sulfonate groups being neutralized with a polycaprolactone polymer being characterized by the formula

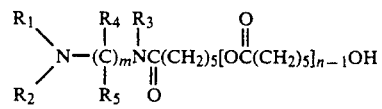

wherein $R_1$ or $R_2$ is an alkyl, cycloalkyl or aryl group; $R_3$, $R_4$ and $R_5$ are a hydrogen or alkyl, cycloalkyl, or aryl groups; m equals 1 to 20 and n equals 1 to 500.

4 Claims, No Drawings

BIODEGRADABLE BARRIER FILMS OF IONOMER POLYMER

This is a divisional of U.S. Ser. No. 131,583 filed Dec. 11, 1987, which is a continuation-in-part of U.S. Ser. No. 883,533, filed July 9, 1986 and now U.S. Pat. No. 4,741,956, issued May 3, 1988.

BACKGROUND OF THE INVENTION

The present invention relates to the compositions of associating polymer protective barrier films which will protect materials, such as agricultural chemicals, for a period of time and then degrade and release the encapsulated contents to the environment. More specifically, this invention relates to the preparation of ionomer compositions containing compatibilized polymers which will be degraded by microorganisms.

It is extremely important today to find an effective means of degrading polymeric materials, which are used in packaging and agricultural films. In the case of mechanical goods, the pollution problem is becoming more severe as used plastic bottles, containers, wrapping film, sheet, etc. accumulate in garbage dumps, along shores, in rivers and other places. There is a great need for some sort of degrading system that will allow the plastic to have a useful life, after which the plastic will degrade into a material that can be handled easily. In other film applications, controlled release of encapsulated materials requires environmental degradation.

This invention provides new polymeric systems capable of degrading to a crumbly friable mass. These systems are based on the ability to produce compatible polymeric films from sulfonated polymers and amine terminated polycaprolactone. The sulfonated polymer can be in the free acid form or neutralized with a metal which can coordinate with the amine. The combination makes excellent coatings, films and mechanical goods due to the compatibilization of the multiple polymer blend. The degradability comes from the inherent characteristic of polycaprolactone, susceptibility to biodegradation.

The advent of plastics has introduced improved methods of packing goods. For example, polyethylene and polypropylene films, bags and bottles and polystyrene foam cups have the advantages of being chemically resistant, mechanically tough, light in weight and inexpensive. However, the increasing use of plastics in packaging has led to the appearance of such materials in litter. While littered plastic articles are no more objectionable than littered articles of other materials, such as paper objects and metal cans, it has been suggested that the impact of plastic litter can be minimized by the development of plastic materials capable of undergoing chemical degradation upon exposure to the natural environment.

Several approaches to the enhancement of the environmental degradability of plastics have been suggested. These include: (1) the incorporation of particulate biodegradable materials, such as starch, as "fillers"; (2) the introduction of photodegradation-sensitizing groups into the molecular structure of a polymer by copolymerization of a common monomer with a second monomer processing such groups; and (3) the incorporation of small amounts of selected additives which accelerate oxidative and/or photo-oxidative degradation. The last approach is particularly attractive for the following reasons. First, the physical properties of the additive-containing composition are extremely similar to those of the base polymer. Second, existing compounding and fabrication processes and equipment can be utilized in the manufacture of finished products; hence, the cost of the finished product should be relatively low. Third, the sensitivity of the composition to environmental degradation can be controlled by proper selection of the type and concentration of additive(s).

The enhancement of the rate of environmental deterioration of plastics through the use of oxidation-promoting additives is known in the prior art. For example, the preparation of degradable polyolefin films containing certain organic derivatives of transition metals is described in U.S. Pat. No. 3,454,510.

Various type additives have been employed in plastic film in order to make the plastic film biodegradable. For example, in U.S. Pat. No. 4,224,416 auto-oxidizable amines are employed. In U.S. Pat. No. 3,994,855 a photolyzable metal compound is employed. U.S. Pat. No. 4,495,311 employs an additive system consisting of a metal compound having at least two valence states and a benzoyl derivative of an organic compound.

The present invention describes a polymer system which is biodegradable in film form. The polymer system of the instant invention comprises a compatible mixture of a sulfonated polymer with an amine terminated polycaprolactone. Compatible mixtures of sulfonated elastomeric polymers and amine terminated polycaprolactones are described in U.S. Pat. No. 4,421,898; however, U.S. Pat. No. 4,421,898 failed to teach or recognize the use of these polymer mixtures in their film form as an agricultural mulch.

SUMMARY OF THE INVENTION

The present invention relates to a process for preparing a plastic film composition which is susceptible to chemical degradation in the environment which comprises preparing a composition comprising a compatible mixture of a sulfonated polymer and an amine terminated polycaprolactone and subsequently subjecting the prepared composition in the form of a polymeric film to a biodegrading environment.

GENERAL DESCRIPTION OF THE INVENTION

The present invention relates to a process for preparing a polymer film composition which is susceptible to chemical degradation in the environment which comprises preparing a composition comprising a compatible mixture of a sulfonated polymer and an amine terminated polycaprolactone and subsequently subjecting the prepared composition in the form of a polymeric film to a biodegrading environment.

The polymeric films of the instant invention are formed from a compatible mixture of a sulfonated elastomeric polymer and an amine terminated polycaprolactone. The sulfonated polymers may be in the free acid form or they can be neutralized salts with metals capable of coordinating amino groups or the sulfonate groups are complexed with a metal ion which is capable of coordinating with the amino group of the polycaprolactone polymer.

The neutralized, sulfonated elastomeric polymers of this present invention are derived from elastomeric or thermoplastic polymers wherein the elastomeric polymers are derived from unsaturated polymers which include low unsaturated elastomeric polymers, such as Butyl rubbers or EPDM terpolymers.

Alternatively, other unsaturated polymers are selected from the group consisting of partially hydrogenated polyisoprenes, partially hydrogenated polybutadienes, Neoprene, styrene-butadiene copolymers or isoprene-styrene random copolymers.

The expression "Butyl rubber" as employed in the specification and claims is intended to include copolymers made from a polymerization reaction mixture having therein from 70 to 99.5 by weight of an isoolefin which has about 4 to 7 carbon atoms, e.g., isobutylene, and about 0.5 to 30% by weight of a conjugated multiolefin having from about 4 to 14 carbon atoms, e.g., isoprene. The resulting copolymer contains 85% to 99.8% by weight of combined isoolefin and 0.2% to 15% of combined multiolefin.

Butyl rubber generally has a Staudinger molecular weight as measured by GPC of about 20,000 to about 500,000, preferably about 25,000 to about 400,000, especially about 100,000 to about 400,000, and a Wijs Iodine No. of about 0.5 to 50, preferably 1 to 15.

For the purposes of this invention, the Butyl rubber may have incorporated therein from about 0.2% to 1.0% of combined multiolefin, preferably about 0.5% to about 6%, more preferably about 1% to about 4%, e.g., 2%.

Illustrative of such a Butyl rubber is Exxon Butyl 365 (Exxon Chemical Company), having a mole percent unsaturation of about 2.0% and a Mooney viscosity (ML, 1+3, 212° F.) of about 40–50.

Low molecular weight Butyl rubbers, i.e., Butyl rubbers having a viscosity average molecular weight of about 5,000 to 85,000 and a mole percent unsaturation of about 1% to about 5% may be sulfonated to produce the polymers useful in this invention. Preferably, these polymers have a viscosity average molecular weight of about 25,000 to about 60,000.

The EPDM terpolymers are low unsaturated polymers having about 1 to about 10.0 weight percent olefinic unsaturation, more preferably about 2 to about 8, most preferably about 3 to 7, defined according to the definition as found in ASTM-D-1418-64 and is intended to mean terpolymers containing ethylene and propylene in the backbone and a diene in the side chain. The preferred polymers contain about 40 to about 75 weight percent ethylene and about 1 to about 10 weight percent of a diene monomer, the balance of the polymer being propylene. Preferably, the polymer contains about 45 to about 70 weight percent ethylene, e.g., 50 weight percent, and about 2.6 to about 8.0 weight percent diene monomer, e.g., 5.0 weight percent. The diene monomer is preferably a nonconjugated diene.

Illustrative of these nonconjugated diene monomers which may be used in the terpolymer (EPDM) are 1,4-hexadiene, dicyclopentadiene, 5-ethylidene-2-norbornene, 5-methylene-2-norbornene, 5-propenyl-2-norbornene, and methyl tetrahydroindene.

A typical EPDM is Vistalon 2504 (Exxon Chemical Company), a terpolymer having a Mooney viscosity (ML, 1+8, 212° F.) of about 40 and having an ethylene content of about 50 weight percent and a 5-ethylidene-2-norbornene content of about 5.0 weight percent. The M-n as measured by GPC of Vistalon 2504 is about 47,000, the Mv as measured by GPC is about 145,000 and the M as measured by GPC is about 174,000.

Another EPDM terpolymer, Vistalon 2504-20, is derived from Vistalon 2504 (Exxon Chemical Company) by a controlled extrusion process, wherein the resultant Mooney viscosity at 212° F. is about 20. The Mn as measured by GPC of Vistalon 2504-20 is about 26,000, the Mv as measured by GPC is about 90,000 and the Mw as measured by GPC is about 125,000.

Nordel 1320 (DuPont) is another terpolymer having a Mooney viscosity at 212° F. of about 25 and having about 53 weight percent of ethylene, about 3.5 weight percent of 1,4-hexadiene and about 43.5 weight percent of propylene.

The EPDM terpolymers of this invention have a number average molecular weight (Mn) as measured by GPC of about 10,000 to about 200,000, more preferably of about 15,000 to about 100,000, most preferably of about 20,000 to about 60,000. The Mooney viscosity (ML, 1+8, 212° F.) of the EPDM terpolymer is about 5 to about 60, more preferably about 10 to about 50, most preferably about 15 to about 40. The Mv as measured by GPC of the EPDM terpolymer is preferably below about 350,000 and more preferably below about 300,000. The Mw as measured by GPC of the EPDM terpolymer is preferably below about 500,000 and more preferably below about 350,000.

The neutralized sulfonated thermoplastic polymers of the instant invention are derived from polystyrene-type thermoplastic polymers which are selected from the group consisting of polystyrene, poly-t-butyl-styrene, polychlorostyrene, polyalpha methyl styrene and co- or terpolymers of the aforementioned with each other and with acrylonitrile or vinyl-toluene.

The polystyrene thermoplastic suitable for use in the practice of the invention have a glass transition temperature from about 90° C. to about 150° C., more preferably about 90° C. to about 140° C. and most preferably about 90° C. to about 120° C. These polystyrene resins have a weight average molecular weight as measured by GPC of about 5,000 to about 500,000, more preferably about 20,000 to about 350,000 and most preferably about 90,000 to about 300,000. These base polystyrene thermoplastic resins can be prepared directly by any of the known polymerization processes. The term "thermoplastic" is used in its conventional sense to mean a substantially rigid (flexus modulus 10,000 psi) material capable of retaining the ability to flow at elevated temperatures for relatively long times.

The preferred polystyrene thermoplastic resin is a homopolymer of styrene having a number average molecular weight of about 180,000 and an intrinsic viscosity in toluene of about 0.8. These polymers are widely available commercially in large volume. A suitable material is Styron 666, which affords a number molecular weight of about 105,000.

In carrying out the invention the polymer is dissolved in a nonreactive solvent, such as a chlorinated aliphatic solvent, chlorinated aromatic hydrocarbon, an aromatic hydrocarbon, or an aliphatic hydrocarbon, such as carbon tetrachloride, dichloroethane, chlorobenzene, benzene, toluene, xylene, cyclohexane, pentane, isopentane, hexane, isohexane or heptane. The preferred solvents are the lower boiling aliphatic hydrocarbons. A sulfonating agent is added to the solution of the elastomeric polymer and nonreactive solvent at a temperature of about −100° C. to about 100° C. for a period of time of about 1 to about 60 minutes, most preferably at room temperature for about 5 to about 45 minutes; and most preferably about 15 to about 30. These sulfonating agents are selected from an acyl sulfate, a mixture of sulfuric acid and an acid anhydride or a complex of a sulfur trioxide donor and a Lewis base containing oxygen, sulfur or phosphorous. Typical sulfur trioxide donors are SO₃, chlorosulfonic acid, fluorosulfonic acid, sulfuric acid, oleum, etc. Typical Lewis bases are dioxane, tetrahydrofuran, tetrahydrothiophene or triethyl phosphate. The most preferred sulfonation agent for this invention is an acyl sulfate selected from the group consisting essentially of benzoyl, acetyl, propionyl or butyryl sulfate. The acyl sulfate can be formed in situ in the reaction medium or pregenerated before its addition to the reaction medium in a chlorinated aliphatic or aromatic hydrocarbon.

It should be pointed out that neither the sulfonating agent nor the manner of sulfonation is critical, provided that the sulfonating method does not degrade the polymer backbone. The reaction is quenched with an aliphatic alcohol, such as methanol, ethanol or isopropanol, with an aromatic hydroxyl compound, such as phenol, a cycloaliphatic alcohol, such as cyclohexanol, or with water. The unneutralized sulfonated elastomeric polymer has about 10 to about 200 meq. unneutralized sulfonate groups per 100 grams of sulfonated polymer, more preferably about 15 to about 100, and most preferably about 20 to about 80. The meq. of unneutralized sulfonate groups per 100 grams of polymer is determined by both titration of the polymeric sulfonic acid and Dietert sulfur analysis. In the titration of the sulfonic acid the polymer is dissolved in solvent consisting of 95 parts of toluene and 5 parts of methanol at a concentration level of 50 grams per liter of solvent. The unneutralized form is titrated with ethanolic sodium hydroxide to an Alizarin-Thymol-phthalein endpoint.

The unneutralized sulfonated polymer is gel free and hydrolytically stable. Gel is measured by stirring a given weight of polymer in a solvent comprised of 95 toluene-5-methanol at a concentration of 5 weight percent for 24 hours, allowing the mixture to settle, withdrawing a weighed sample of the supernatant solution and evaporating to dryness.

Hydrolytically stable means that the acid function, in this case the sulfonic acid, will not be eliminated under neutral or slightly basic conditions to a neutral moiety which is incapable of being converted to highly ionic functionality.

Neutralization of the unneutralized sulfonated polymer can be accomplished by the addition of a solution of a polycaprolactone polymer to the unneutralized sulfonated elastomeric polymer typically dissolved in the mixture of the aliphatic alcohol and nonreactive solvent. The polycaprolactone polymer is dissolved in a solvent system consisting of toluene, optionally containing an aliphatic alcohol. These polycaprolactone polymers are formed by the reaction of ε-caprolactone with an organic diamine in the presence of a catalyst as described in U.S. Pat. No. 4,421,898. The anhydrous ε-caprolactone and the organic diamine in the presence of the catalyst are reacted together in a reaction vessel in the absence of a solvent at a temperature of about 50° to about 200° C., more preferably about 75° to about 180° C. and most preferably about 90° to about 100° C. for a sufficient period of time to effect polymerization.

The reaction of ε-caprolactone with the diamine can generally be depicted by the equation:

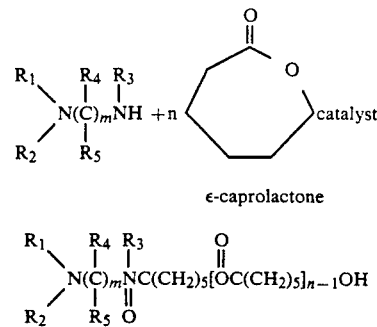

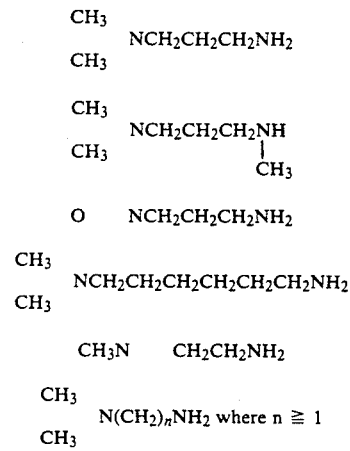

wherein n=1 to 500; m=1 to 20; $R_1$ or $R_2$ are selected from the group consisting of alkyl and cycloalkyl groups having about 1 to about 20 carbon atoms, more preferably about 1 to about 12 carbon atoms, and aryl groups; $R_3$ is selected from the group consisting of hydrogen, alkyl and cycloalkyl groups having about 1 to about 20 carbon atoms, more preferably about 1 to about 12, and aryl groups; and $R_4$ and $R_5$ are hydrogen, alkyl, cycloalkyl or aryl groups. Typical but nonlimiting examples of useful diamines are:

$$\begin{array}{c} CH_3 \\ \phantom{CH_3}\diagdown \\ \phantom{CH_3}\phantom{x}NCH_2CH_2CH_2NH_2 \\ \phantom{CH_3}\diagup \\ CH_3 \end{array}$$

$$\begin{array}{c} CH_3 \\ \phantom{CH_3}\diagdown \\ \phantom{CH_3}\phantom{x}NCH_2CH_2CH_2NH \\ \phantom{CH_3}\diagup \phantom{xxxxxxxxxx} | \\ CH_3 \phantom{xxxxxxxxxx} CH_3 \end{array}$$

$$O \quad NCH_2CH_2CH_2NH_2$$

$$\begin{array}{c} CH_3 \\ \phantom{CH_3}\diagdown \\ \phantom{CH_3}\phantom{x}NCH_2CH_2CH_2CH_2CH_2CH_2NH_2 \\ \phantom{CH_3}\diagup \\ CH_3 \end{array}$$

$$CH_3N \quad CH_2CH_2NH_2$$

$$\begin{array}{c} CH_3 \\ \phantom{CH_3}\diagdown \\ \phantom{CH_3}\phantom{x}N(CH_2)_nNH_2 \text{ where } n \geq 1 \\ \phantom{CH_3}\diagup \\ CH_3 \end{array}$$

Catalysts useful in the promotion of the above-identified reaction are selected from the group consisting of stannous octanoate, stannous hexanoate, stannous oxalate, tetrabutyl titanate, a variety of metal organic based catalysts, acid catalyst and amine catalysts, as described on page 266 and forwarded in a book chapter authored by R.D. Lundberg and E.F. Cox entitled *Kinetics and Mechanisms of Polymerization: Ring Opening Polymerization.* edited by Frisch and Rugen, published by Marcell Dekker in 1969, wherein stannous octanoate is an especially preferred catalyst. The catalyst is added to the reaction mixture at a concentration level of about 100 to about 10,000 parts of catalyst per one million parts of ε-caprolactone.

The resultant polycaprolactone polymer has an Mn as measured by GPC of about 200 to about 50,000, more preferably about 500 to about 40,000, and most preferably about 700 to about 30,000, and a melting point from below room temperature to about 55° C., more preferably about 20° C. to about 52° C., and most preferably about 20° C. to about 50° C.

The metal sulfonate-containing polymers at the higher sulfonate levels possess extremely high melt viscosities and are thereby difficult to process. The addition of ionic group plasticizers markedly reduces melt viscosity and frequently enhances physical properties.

To the neutralized sulfonated polymer is added, in either solution or to the crumb of the unneutralized form of the sulfonated polymer, a preferential plasticizer selected from the group consisting of carboxylic acids having about 5 to about 30 carbon atoms, more preferably about 8 to about 22 carbon atoms, or basic salts of these carboxylic acids, wherein the metal ion of the basic salt is selected from the group consisting of aluminum, ammonium, lead or Groups IA, IIA, IB, and IIB of the Periodic Table of Elements and mixtures thereof. The carboxylic acids are selected from the group consisting of lauric, myristic, palmitic or stearic acids and mixtures thereof, e.g., zinc stearate, magnesium stearate or zinc laurate.

The preferential plasticizer is incorporated into the neutralized sulfonated polymer at less than about 60 parts by weight per 100 parts of the sulfonated polymer, more preferably at about 5 to about 40, and most preferably about 7 to about 25. Alternatively, other preferential plasticizers are selected from ureas, thioureas, amines, amides, ammonium and amine salts of carboxylic acids and mixtures thereof. The preferred plasticizers are selected from fatty acid or metallic salts of fatty acid and mixtures thereof. The resultant neutralized sulfonated polymer with preferential plasticizer is isolated from the solution by conventional steam stripping and filtration.

The biodegradable films or coatings of the instant invention are formed by applying the organic solution of the sulfonated ionomer (e.g., zinc sulfo EPDM with 25 meq. of sulfonate grup) and of the amine terminated caprolactone (e.g., poly-$\epsilon$ caprolactone 3-dimethyl amino propylamine) over a substrate at ambient temperature or at 10°-70° C. by either dip-coating or spray-coating or with the use of other techniques for thin spreading (such as brushing). The organic solution can be prepared by mixing a proportionate weight of about 1-10% ZSE-25 with 1-10% poly-$\epsilon$ caprolactone 3-dimethyl amino propylamine, both in Solvent A. Solvent A comprises 85-97.5% toluene or other appropriate hydrocarbon and 15-2.5% methanol or other alcohol. The organic solvent is permitted to evaporate with or without the aid of forced drying gas, such as nitrogen gas. This step is called the drying process. The drying gas can be from ambient temperature up to the boiling point of the organic solvent system. Preferably, the temperature of the drying gas is between 20° C. and 100° C. The most preferred temperature of the drying gas should be about 70° C. for fast evaporation of the organic solvent system. After drying the thickness of the applied film or coating should be about 2 to about 100 micrometers. Most preferred, the coating thickness should be about 2 to about 20 micrometers for both performance and economic reasons. To control the thickness of the film or coating the solution of this instant invention is applied at 0.5 to 6 weight percent. Most preferably, the concentration should be about 5 weight percent. The film of this instant invention can be applied in single or multiple layers, depending on the desired film or coating thickness. In any instance the organic solvent system is evaporated after each layer application. The biodegradable polymer film or coating can be applied over the substrate or over a previous coating. In the latter case, such practice can modify or improve the performance of the coated system.

The film of the instant invention can be used as barrier or controlled release coating for applications such as inorganic or organic fertilizers, micronutrients, herbicides or other solid materials.

Urea or other water soluble fertilizer granules can be coated to maximize the plant uptake of the applied fertilizer through the minimization of losses, including vaporation, nitrogen fixation and leaching. The use of the instant polymer system as a coating on urea or other water soluble fertilizers permits the user to form very thin defect free films of about 2 to about 100 micrometers on a very rough surface such as ureas or other water soluble fertilizers. The coating of urea can be achieved by spraying a solution of the instant invention onto a cascading stream of urea granules through an appropriate technique, such as fluidized bed coating. Examples of fluidized bed coating processes are: conventional spray coating wherein the solid particulates are coated by spraying the coating solution above or below the bed; a Wurster configuration; or a fluidized bed with a rotating bed support plate. It is envisioned that coated urea or other fertilizer particulates can be utilized in a variety of environmental conditions and yet the release of nitrogen or other water soluble nutrients can be controlled in such a way that they are available when the target plant (e.g., cereal) needs them. With the film of this instant invention, exposure time for microbial degradation of the polymer or ionomer and amine terminated $\epsilon$-caprolactone complex can range from several weeks to about 10 months.

The polymers of the instant invention can be extruded into polymeric films of about 0.5 to 40 mils thick, wherein these films which can be pigmented with a pigment can be readily used as an agricultural mulch film, wherein the polymeric film is self-supporting and not supported by a substrate and is substantially free of pin holes.

DESCRIPTION OF THE PREFERRED EMBODIMENTS

The following Examples illustrate the present invention without, however, limiting the same hereto.

Unless otherwise specified, all measurements are in parts by weight per 100 parts of sulfonated polymers.

EXAMPLE 1

3.5 g (1 meq.) of a sulfonated EPDM (based on EPDM of 50% ethylene, 45% propylene and 5% ENB, sulfonated with acetyl sulfate in situ, as described in U.S. Pat. No. 4,221,712 and related cases, isolated in methanol as the acid form, and dried in a vacuum oven at 35° C.), containing 29.0 meq. of sulfur per 100 g of polymer, as determined by elemental analysis, was dissolved in 66.5 toluene overnight to give a 5.0 weight percent solution.

2.1 g (1 meq.) of an N,N-dimethyl-1,3-propane diamine terminated polycaprolactone, molecular weight 2,100% N=1.314±0.005% was dissolved in 18.9 g of toluene to give a 10.0 weight percent solution. This solution was then added to the highly viscous EPDM polymer sulfonic acid solution prepared above.

Films were cast from the solution of neutralized polymer acid onto Teflon coated aluminum foil. The solvent was removed by evaporation at ambient conditions. The resultant films were a slightly hazy yellow and showed no visible signs of phase separation. The resulting films appeared to be tough and flexible, with no evidence in incompatibility.

Thermal mechanical analysis conducted on the polymer sample revealed a major transition at about −65° C. (EPDM Tg) and a second transition at about 38° C., identified as the crystalline melting point for the polycaprolactone phase.

EXAMPLE 2

3.5 g (1 meq.) of a sulfonated EPDM (similar to that of Example 1) sulfonated with acetyl sulfate in situ, isolated in methanol, as the acid form, and dried in a vacuum oven at 35° C.) containing 29.0 meq. of sulfur per 100 g of polymer, as determined by elemental microanalysis was dissolved in 66.5 g toluene overnight to give a 5.0 weight percent solution.

3.98 g (1 meq.) of an N,N-dimethyl-1,3-propane diamine terminated polycaprolactone molecular weight 3,980% N=0.682±0.003% was dissolved in 35.8 g toluene to give a 10.0 weight percent solution. This solution was then added to the highly viscous EPDM polymer sulfonic acid solution prepared above.

Films were cast from the final solution of the neutralized polymer acid using Teflon coated aluminum foil pans as the substrate. The solvent was removed by evaporation at ambient temperature. These films did not phase separate, but were hazier and stiffer than those prepared under Example 1.

EXAMPLE 3

The following Example will demonstrate the performance of the coating of ionomer and amine terminated-caprolactone complex.

Two polymer coating systems were prepared in 97.5/2.5 toluene-methanol solvent. Polymer coating system A contains 2 weight percent zinc sulfo EPDM (ZSE-25) and poly-ε-caprolactone 3-dimethyl amino propylamine (molecular weight=1,000) at 9/1 ratio of the former to the latter. Polymer coating system B also contains 2 weight percent of zinc sulfo EPDM (ZSE-25) and poly-ε-caprolactone 3-dimethyl amino propylamine, but with the molecular weight of the latter of about 6,000; also at similar 9/1 ratio of the former to the latter. These solutions were used for cast coating of the film of this instant invention over solid, dry urea samples in order to determine the barrier properties of the encapsulated urea to water extraction.

To determine barrier properties of films formed from solution, urea slides were coated for immersion tests. The procedures for preparing coated samples of urea slides and conducting immersion tests are described below.

Urea samples were prepared by depositing reagent grade urea (Fisher Scientific) over microscope glass slides. This was done by dipping glass slides into molten urea at a temperature of about 135°–145° C., followed by cooling and solidification of the urea layer. The urea layer was built up to about 7 mm by four to five successive dipping and cooling cycles. These urea samples were then coated by a polymeric film using a second dipping procedure. Urea slides were repeatedly dipped into polymer solutions, such as those described above, followed by drying in a vacuum oven at 70° C. for about 3 hours. The dipping and drying cycles were repeated until the film thicknesses shown in Table I were obtained.

The barrier properties of the various polymeric films were determined by immersion of each coated urea slide in about 100 g of deionized water at room temperature. The amount of urea released into the water was determined by recovering the urea after evaporating the water. Each sample was initially immersed for 1 day, followed by immersion in fresh water for 3 days and for weekly intervals thereafter.

Table I shows the permeabilities of urea solution extracted from the coated slides which were immersed in water at room temperature. The permeabilities of the coating materials were determined by applying Fick's law of diffusion at steady state. Fick's law states that:

$$J_m = DA \frac{\Delta c}{\delta}$$

where $J_m$=mass flux (loss) through the film or membrane, A=transport area, $\Delta C$=concentration gradient, $\delta$=film or membrane thickness and D=membrane diffusivity constant which is equal to the ratio of permeability (P) over the solubility ratio (K) of urea in the membrane and in water.

The performance of the ionomer coatings was compared with that of two commercially used coating materials. The first commercial coating solution was a tung oil solution made by Formby of Mississippi at 30 weight percent solids in petroleum distillate. The second commercial coating solution was linseed oil modified polyurethane Type I made by Minwax Paint Co. of New Jersey at 45% solids in petroleum distillate. The two commercial coatings were cured at 70° C. for 48 hours after coating.

The permeability of urea solution through the films of this instant invention was found to be as low or lower than either that of tung oil or that of polyurethane. Tung oil and polyurethane were disclosed as release control coatings for water soluble fertilizers in U.S. Pat. No. 3,321,298 and U.S. Pat. No. 3,223,518.

The reason for scatter in the permeability data for biodegradable polymer coatings shown in Table I is believed to be a result of the coating qualify. Existence of pin holes will increase the apparent permeability as calculated above. One should, therefore, assume that the lowest number corresponds to a more perfect coating. Permeabilities for the other polymers in Table I do, on the other hand, agree with literature data for perfect coatings.

This Example shows that encapsulated urea having a coating of the instant invention is more resistant to water extraction than the urea encapsulated by commercially used coatings. One can, therefore, apply a thinner coating of the ionomer and amine terminated ε-caprolactone for equivalent results to obtain cost advantage of the coating of the instant invention can be useful for slower release until microbial degradation takes place for complete release of the urea.

TABLE I

| Sample No. | Coating Material | Film Thickness Microns | Permeability (P = DK) cm²/sec |
|---|---|---|---|
| 141-3 | Tung Oil | 75 | $4.3 \times 10^{-9}$ |
| 141-6 | Tung Oil | 125 | $7.6 \times 10^{-9}$ |
| 158-4 | Polyurethane | 100 | $1.3 \times 10^{-9}$ |
| 158-5 | Polyurethane | 40 | $2.1 \times 10^{-9}$ |
| 157-3 | Polymer Coating System A | 20 | $6 \times 10^{-10}$ |
| 157-4 | Polymer Coating System B | 30 | $1.8 \times 15^{-9}$ |

What is claimed is:

1. An encapsulated water soluble fertilizer which comprises a polymeric film of about 2 to about 100 micrometers coated on a surface of said fertilizer, said polymeric film comprising a sulfonated polymer having about 10 to about 200 meq of sulfonate groups per 100 grams of said sulfonated polymer, said sulfonate groups being neutralized with a polycaprolactone polymer being characterized by the formula

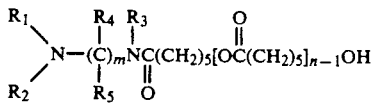

wherein $R_1$ or $R_2$ is an alkyl, cycloalkyl or aryl group; $R_3$, $R_4$ and $R_5$ are a hydrogen or alkyl, cycloalkyl, or aryl groups; m equals 1 to 20 and n equals 1 to 500.

2. An encapsulated water soluble fertilizer which comprises a polymeric film of about 2 to about 10 micrometers coated on a surface of said fertilizer, said polymeric film comprising a sulfonated polymer having about 10 to about 200 meq of sulfonate groups per 100 grams of said sulfonated polymer, said sulfonate groups complexed with a metal ion which is capable of coordinating with the amino group of a polycaprolactone polymer being characterized by the formula

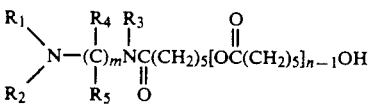

wherein $R_1$ or $R_2$ is an alkyl, cycloalkyl or aryl group; $R_3$, $R_4$ and $R_5$ are a hydrogen or alkyl, cycloalkyl, or aryl groups; m equals 1 to 20 and n equals 1 to 500.

3. An encapsulated water soluble micronutrient which comprises a polymeric film of about 2 to about 100 micrometers coated on a surface of said micronutrient, said polymeric film comprising a sulfonated polymer having about 10 to about 200 meq of sulfonate groups per 100 grams of said sulfonated polymer, said sulfonate groups being neutralized with a polycaprolactone polymer being characterized by the formula

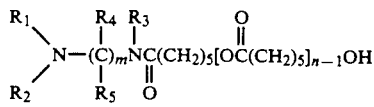

wherein $R_1$ or $R_2$ is an alkyl, cycloalkyl or aryl group; $R_3$, $R_4$ and $R_5$ are a hydrogen or alkyl, cycloalkyl, or aryl groups; m equals 1 to 20 and n equals 1 to 500.

4. An encapsulated water soluble micronutrient which comprises a polymeric film of about 2 to about 100 micrometers coated on a surface of said micronutrient, said polymeric film comprising a sulfonated polymer having about 10 to about 200 meq of sulfonate groups per 100 grams of said sulfonated polymer, said sulfonate groups complexed with a metal ion which is capable of coordinating with the amino group of a polycaprolactone polymer being characterized by the formula

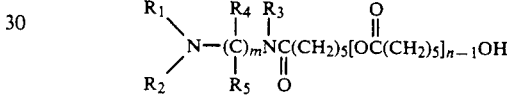

wherein $R_1$ or $R_2$ is an alkyl, cycloalkyl or aryl group; $R_3$, $R_4$ and $R_5$ are a hydrogen or alkyl, cycloalkyl, or aryl groups; m equals 1 to 20 and n equals 1 to 500.

* * * * *